(12) United States Patent
Schweitzer

(10) Patent No.: US 8,880,142 B2
(45) Date of Patent: Nov. 4, 2014

(54) METHOD FOR PRECISELY DETERMINING THE FLUORESCENCE IN A LAYER SYSTEM, SUCH AS THE EYE

(75) Inventor: Dietrich Schweitzer, Neustadt/Orla (DE)

(73) Assignee: Heidelberg Engineering GmbH, Heidelberg (DE)

( * ) Notice: Subject to any disclaimer, the term of this patent is extended or adjusted under 35 U.S.C. 154(b) by 372 days.

(21) Appl. No.: 13/060,656

(22) PCT Filed: Sep. 3, 2009

(86) PCT No.: PCT/DE2009/001249
§ 371 (c)(1),
(2), (4) Date: Feb. 24, 2011

(87) PCT Pub. No.: WO2010/025715
PCT Pub. Date: Mar. 11, 2010

(65) Prior Publication Data
US 2011/0152693 A1     Jun. 23, 2011

(30) Foreign Application Priority Data
Sep. 3, 2008 (DE) .......................... 10 2008 045 886

(51) Int. Cl.
*G01N 21/64* (2006.01)
*G01N 33/58* (2006.01)

(52) U.S. Cl.
CPC .......... *G01N 21/6408* (2013.01); *G01N 33/582* (2013.01); *G01N 2021/6439* (2013.01)
USPC ............................. 600/407; 600/473; 600/476

(58) Field of Classification Search
CPC .............. G01N 21/64; G01N 21/6408; G01N 21/6456; A61B 3/12; A61B 5/1225; A61B 3/10; A61B 3/1005; A61B 3/1015; A61B 5/0059; A61B 5/0071

USPC .......................................... 600/476, 407, 473
See application file for complete search history.

(56) References Cited

U.S. PATENT DOCUMENTS 5,984,474 A * 11/1999 Schweitzer et al. .......... 351/205
6,304,771 B1 * 10/2001 Yodh et al. .................... 600/476
(Continued)

FOREIGN PATENT DOCUMENTS

WO     WO-2006/009910     1/2006

OTHER PUBLICATIONS

Schweitzer, D. et al., "Method for simultaneous detection of functionality and tomography"; Prceedings of the SPIE—The International Society for Optical Engineering SPIE—The Inernational Society for Optical Engineering USA, vol. 7368, 2009, pp. 736804-1-136804-9, XP002568108.

(Continued)

*Primary Examiner* — Unsu Jung
*Assistant Examiner* — Michael Kellogg
(74) *Attorney, Agent, or Firm* — Jordan and Hamburg LLP

(57) ABSTRACT

Determining the fluorescence in a layer system, such as the eye. The summary decay behavior of the fluorescence is evaluated. Points of origin of individual fluorescence of the layer system are determined. The time of origin (tci) of each fluorescence in the individual layers of the layer system are determined using layer-specific, time-dependent parameters for the relevant fluorescence. The parameters indicate the time of origin of the fluorescence in the relevant layer. The parameters are used in a model function for calculating the summary decay behavior of the fluorescence.

6 Claims, 2 Drawing Sheets

(56) References Cited

U.S. PATENT DOCUMENTS

2002/0158212 A1* 10/2002 French et al. ............. 250/459.1
2007/0197894 A1* 8/2007 Jo et al. ......................... 600/407

OTHER PUBLICATIONS

Mycek, M. A. et al., "Simulations of time-resolved fluorescence in multilayered biological tissues: applications to clinical data modeling"; Proceedings of the SPIE—The International Society for Optical Engineering SPIE—Int. Soc. Opt. Eng. USA, vol. 4958, 2003, pp. 51-59, XP002568109.

Vishwanath, K. et al., "A Monte-Carlo model for time-resolved fluorescence from a two-layered turbid medium"; OSA Trends in Optics and Photonics, Washington, DC, US, vol. 88, Jan. 1, 2003, pp. 832-834, XP009129341.

Pfefer, T.J. et al., "Computational modeling of device-tissue interface geometries for time-resolved fluorescence in layerd tissue"; Proceedings of the SPIE—The International Society for Optical Engineering SPIE—The International Society for Optical Engineering USA, Vo. 6083, No. 1, Feb. 9, 2006, pp. 1-9, XP002568110.

Schweitzer, D. et al., "In vivo measurement of time-resolved autofluorescence at the human fundus"; Journal of Biomedical Optics Nov./Dec. 2004 SPIE US, vol. 9, No. 6, Nov. 2004, pp. 1214-1222, XP002568111.

Schweitzer, D. et al., "Comparison of time-resolved autofluorescence in the eye-ground of healthy subjects and patients suffering from age-related macular degeneration"; Proceedings of the SPIE—The International Society for Optical Engineering SPIE—Int. Soc. Opt. Eng USA, vol. 5862, No. 1, 2005, pp. 58620R-1-58620R-12, XP002568112.

Schweitzer, D. et al., "Towards Metabolic Mapping of the Human Retina"; Microscopy Research and Technique, 70, pp. 410-419, 2007.

Koenig, Karsten et al., "High-resolution muliphoton tomography of human skin with subcellular spatial resolution and picosecond time resolution"; Journal of Biomedical Optics, vol. 8, No. 3, Jul. 2003, pp. 432-439.

Denk, Winfried et al., "Two-Photon Laser Scanning Fluorescence Microscopy"; Science, vol. 248, Apr. 6, 1990, pp. 73-76.

Masters, Barry R. et al., "Multiphoton Excitation Microscopy of In Vivo Human Skin—Functional and Morphological Optical Biopsy Based on Three-Dimensional Imaging, Lifetime Measurements and Fluorescence Spectroscopy"; Annals New York Academy of Sciences, vol. 838, pp. 58-67, 1998.

Ruechmann, A. von et al., "Distribution of fundus autofluorescence with a scanning laser ophthalmoscope"; British Journal of Ophthalmology, 1995, 79, pp. 407-412.

Holz, Frank G. et al., "Fundus Autofluorescence and Development of Geographic Atrophy in Age-Related Macular Degeneration"; IOVS, Apr. 2001, vol. 42, No. 5, pp. 1051-1056.

Delori, Francois C. et al., "In Vivo Fluorescence of the Ocular Fundus Exhibits Retinal Pigment Epithelium Lipofuscin Characteristics"; Investigative Ophthalmology & Visual Science, Mar. 1995, vol. 36, No. 3, pp. 718-729.

* cited by examiner

METHOD FOR PRECISELY DETERMINING THE FLUORESCENCE IN A LAYER SYSTEM, SUCH AS THE EYE

BACKGROUND OF THE INVENTION

The present invention relates to a method for precisely determining the fluorescence in a layer system, such as the eye.

The method can be used for observing the layer-specific fluorescence behavior of endogenous or exogenous fluorophores in organs of biological objects, such as the eye, the skin, the intestine, and the bladder. This invention allows for the control of the diffusion of marked pharmaceuticals through morphological structures and their accumulation at target structures. It can also be used for examining the fluorescence in layered plant structures.

By the invention, a tomographic reconstruction of an object having a structure of fluorescent layers is obtained. The manufacturing control in the production of products with a layered structure is possible, too.

If layer systems are excited to fluorescence, local fluorophores emit in the individual layers in dependence on the specific layer structure, and it is known that the summary decay behavior of the summary fluorescence is observed to evaluate the fluorescence of said fluorophores. In particular, in the human eye, fluorophores are excited in the anatomic layers of the front eye and in the layers of the eye background. The fluorescence both of endogenous fluorophores and of fluorescent markers can be used for diagnostic purposes, such as the assessment of the metabolic state. Thus, the fluorescence analysis of the eye provides information that can be very important for ophthalmologic examinations and for assessing the state of the eye and possible damages and/or for the early detection of diseases of the eye or its components. This information refers to the evaluation of the decay behavior of the substance-specific functional information obtained from the complete object, such as the eye. Moreover, there is still the unresolved problem of gathering information on the layer-specific points of origin of the substance-specific fluorescence.

In addition to this, it would be useful if such measurements and evaluations could be directly performed in the clinical routine of ophthalmological examinations with as little effort and as precise results as possible.

However, the invention is not restricted to applications related to the eye as a layer system.

Generally, the measurements of fluorescence in mixtures of fluorophores are based on the assumption that the substances to be analyzed are located in the same object plane. This assumption applies both for the examination of endogenous fluorophores and of fluorescent markers in cell or tissue cultures.

By means of 2-photon or multi-photon excitation (K. Konig, I. Riemann: High-resolution multi-photon tomography of human skin with subcellular spatial resolution and picosecond time resolution. Journal of Biomedical Optics 8(3), 2003, 432-439), single points of one layer of an object can be excited to fluorescence with a high geometric resolution. In combination with scanning systems (scanner microscopes) the fluorescence of a complete layer can be determined (W. Denk, J. H. Strickler, W. W. Webb: Two-photon laser scanning microscopy, Science 248, 1990, 73-76; B. R. Masters, P. T. C. So, E. Gratton: Multiphoton excitation fluorescence microscopy of in vivo human skin. Ann. N.Y. Acad. Sci. 838, 1998, 58-67). After focusing on further layers, the geometric structure of the fluorescent layers of an object can be principally determined.

To obtain the energy density required for the 2-photon or multi-photon excitation in the focus of the excitation system, optical systems with a high numeric aperture are necessary for high radiation performances. For this purpose immersion objectives of microscopes are useful. They can analyze the fluorescent layers of a microscopic specimen or of the skin up to a layer thickness of about 1 mm in a small field.

For strongly absorbing structures, such as the retinal pigment epithelium, a damage will be already caused if the applied radiation energy is only higher by the factor 3 than the energy used for exciting the fluorescence. The low aperture of the eye determined by the opened iris and the focal length of the eye also excludes the use of 2-photon or multi-photon processes for analyzing the fluorescence of the eye background in the living eye.

The simultaneous determination of the fluorescence of different layers of an object is principally not possible by means of the 2-photon or multi-photon excitation because focusing with high precision can only be realized in one focal plane. Thus, the 2-photon or multi-photon excitation normally does not allow the simultaneous fluorescence measurement of different layers of the eye, for example, of the front and back eye segment.

The examination of the autofluorescence or of the fluorescence of exogenous markers can be carried out at the eye by using a fundus camera or laser scanner ophthalmoscopes. The state-of-the-art is the measurement of static fluorescence, mainly of the eye background (A. von Rückmann, F. W. Fitzke, A. C. Bird: Distribution of fundus autofluorescence with a scanning laser ophthalmoscope, Br. J Ophthalmol 79, 1995, 407-412; F. G. Holz et al.: Fundus autofluorescence and development of geographic atrophy in age-related macular degeneration. Invest Ophthalmol Vis Sci 42, 2001, 1051-1056). By combining a modified ophthalmoscope with a spectrograph, the fluorescence spectrum of a selected area of the eye background can be calculated (F. C. Delori et al.: In vivo fluorescence of the ocular fundus exhibits retinal pigment epithelium lipofuscin characteristics. Invest Ophthalmol Vis Sci 36, 1995, 718-729; D. Schweitzer et al.: Die altersabhängige Makulopathie—Vergleichende Untersuchungen zwischen Patienten, deren Kindern and Augengesunden. (The age-related maculopathy—Comparative examinations of patients, their children and persons with healthy eyes.) Ophthalmologe 97, 2000, 84-90).

In more recent developments, the dynamic fluorescence of the eye is measured after excitation by ps-laser pulses (D. Schweitzer et al.: In vivo measurement of time-resolved autofluorescence at the human fundus. J Biomed Opt 9, 2004, 1214-1222; D. Schweitzer et al.: Towards metabolic mapping of the human retina. Microscopy Research and Tech-nique 70, 2007, 410-419). In this method it is assumed for the evaluation of the dynamic (time-resolved) fluorescence of the eye (D. Schweitzer et al.: In vivo measurement of time-resolved autofluorescence at the human fundus, J Biomed Opt 9, 2004, 1214-1222) or of other objects that the fluorescence of all fluorophores has its origin in the same focal plane. A multi-exponential model function according to the equation (1) is, for example, used for the approximation of the summary decay behavior of the fluorescence of the eye as a layer system:

$$\frac{I(t)}{I_0} = \sum_{i=1}^{p} \alpha_i \cdot e^{-\frac{t}{\tau_i}} + b \quad (1)$$

wherein
$I_o$: maximum fluorescence intensity
$I(t)$: fluorescence at the time t
$\tau_i$: decay time of the component i
$\alpha_i$: pre-exponential factor i
b: underground intensity.

Since it is assumed in this model function that all fluorophores are localized in only one layer, it is not possible to ascertain the points of origin of the individual fluorescence. Consequently, the time-dependent summary fluorescence of an object that contains several fluorescent layers can be approximately evaluated, but this evaluation is not reliable and inaccurate.

SUMMARY OF THE INVENTION

The object of the invention is to provide a method that is simple and requires as little effort as possible for evaluating the fluorescence in a layer system, and that allows evaluation of the summary decay behavior of the fluorescence very precisely and a determination of the points of origin of the individual fluorescence of the layer system at the same time.

According to the invention, each of the times of origin of the fluorescence are determined in the individual layers of the layer system for evaluating the summary decay behavior of the time-resolved fluorescence of the layer system by considering the layer-specific, time-dependent parameters for the relevant fluorescence in the model function for the approximation to the measured course of the summary decay behavior, and said parameters indicate the time of origin of the fluorescence in the layer of interest. In this way it is possible to evaluate the summary decay behavior of the time-resolved fluorescence of the layer system considering the times of origin in the individual layers of the layer system.

The layer-specific time-dependent parameters can be included in said model function, for example, as fit parameters tc. An example for a multi-exponential fit shows the general equation (2)

$$\frac{I(t)}{I_0} = \sum_{i=1}^{p} \alpha_i \cdot e^{-\frac{t-tc_i}{\tau_i}} + b \quad (2)$$

with $$e^{-\frac{t-tc_i}{\tau_i}} = 0$$

for $t < tc_i$ and
$I_o$: maximum fluorescence intensity
$I(t)$: fluorescence at the time t
$\alpha_i$: pre-exponential factor i
$\tau_i$: decay time of the component i in layer i
$tc_i$: time of the generation of fluorescence in layer i
b: underground intensity.

Simultaneously, it is advantageously possible to calculate the local distance of the points of origin of the fluorescence from these gained layer-specific, time-dependent parameters, which represent the times of origin of the single fluorescence of the layer system, by multiplying the difference of these parameters with the light speed in the relevant layer. On the basis of these local distances the absolute points of origin of the fluorescence can be determined in the simplest way. Therefore, the invention additionally allows a determination, apart from the above described more precise evaluation of the summary decay behavior of the time-resolved fluorescence of the layer system, the point of origin of the fluorescence in the geometric structure of the layer system. This task has heretofore been an unresolved issue.

By the invention it can be distinguished whether a multi-exponential fluorescence decay behavior exists in a layer or whether a summary multi-exponential decay behavior has been developed by the decay behavior of fluorophores in single layers.

For applications in ophthalmology, at least a difference can be made between the fluorescence of the eye lens, the retina and the retinal pigment epithelium. As statements can be received about the cellular metabolic state on the basis of time-resolved autofluorescence, if possible, in combination with adjustable spectral excitation and detection of the time-resolved fluorescence in different spectral ranges, this invention allows a determination of changes in the metabolic state in single functional layers of the eye or of other optically accessible organs.

The invention is not restricted to the detection of autofluorescence in single layers, in particular, not to the evaluation of summarily obtained decay behaviors of autofluorescence. It can also be applied for the analysis of time-dependent fluorescence of external markers in layer systems, even in combination with endogenous fluorophores. For example, it is possible to find out in which layer of the object a fluorescent marker substance accumulates. Additionally, the local progression of the diffusion of a tropically applied fluorescent marker can be determined as a function of time. Thus, the local change of a fluorescent drug or of a drug provided with markers can be determined as a function of time, for example, in the diffusion of topically applied pharmaceuticals through the glass body of the eye. This aspect is of interest in pharmacokinetic examinations.

Since the decay time of a fluorophore changes, for example, if it binds to a protein, the reaction of a drug in the corresponding anatomic layer can also be assessed by this invention.

In the following the invention is explained in more detail by the embodiment represented in the figures.

DETAILED DESCRIPTION OF THE INVENTION

Figure 1:
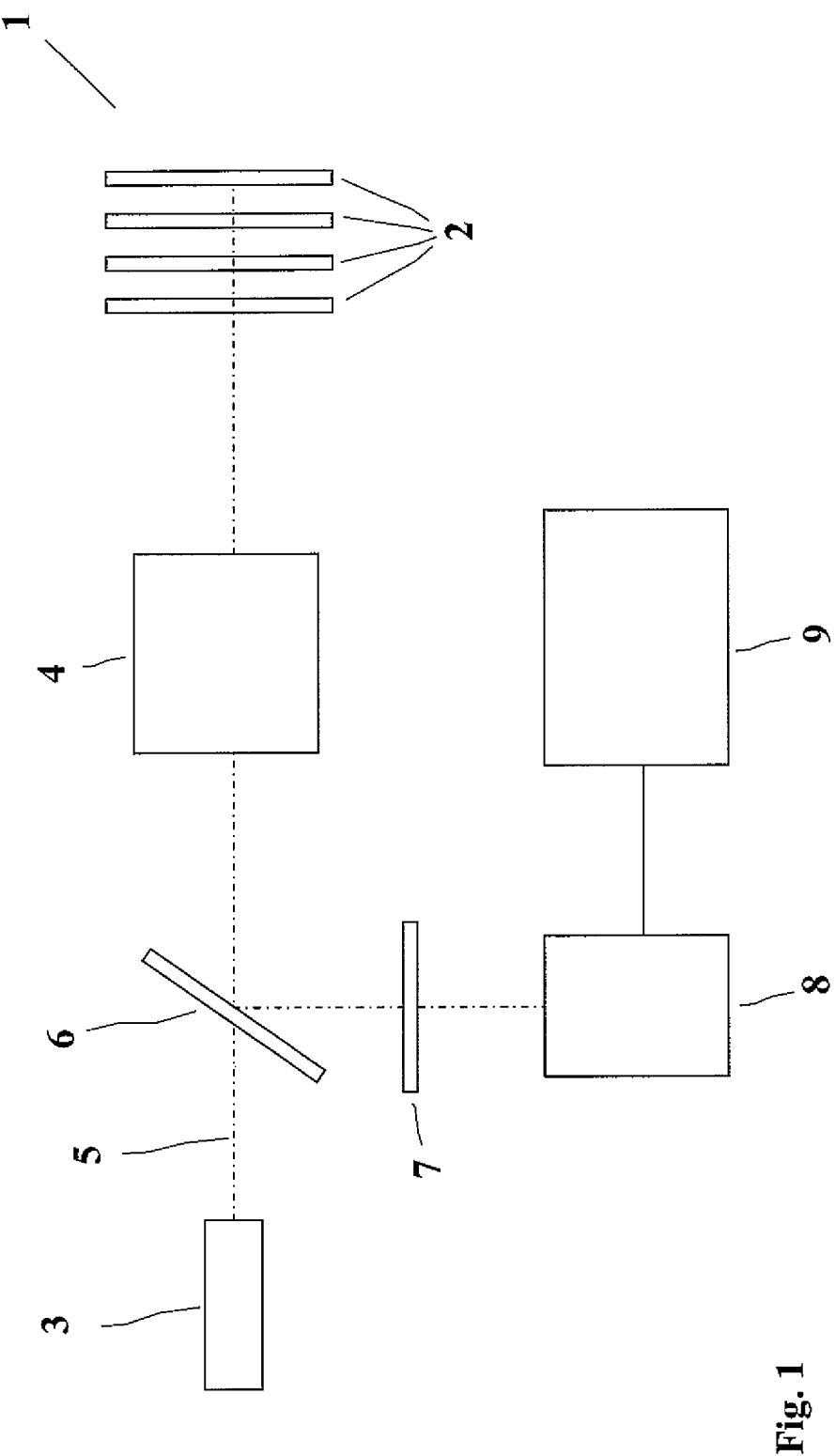
FIG. 1 is a schematic representation of an arrangement for measuring the time-resolved fluorescence of an object having fluorescent layers.

A laser scanner ophthalmoscope is used to serially excite to fluorescence all points of a field, which is to be analyzed in the fluorescence and is part of an object (for example of an eye) consisting of fluorescent layers 2, by illuminating said field with a pulsed laser 3 during the spectrometric scanning by a scanner system 4. In this method, each of the layers 2 along the direction of propagation of an excitation beam 5 of the pulsed laser 3 is excited by the same excitation beam 5 that reaches the object via a dichroitic mirror 6 and the scanner system 4. The fluorescence light generated by this fluorescence excitation and recorded by the scanner system 4 is guided by the dichroitic mirror 6 to a block filter 7 that separates said fluorescent light from the excitation light. After this separation, the time-resolved fluorescent light is summarily detected from all fluorescent layers 2 of the object 1 in a unit 8 for the time-resolved detection of the fluorescent light (for example by means of the single photon counting method known per se).

Figure 2:
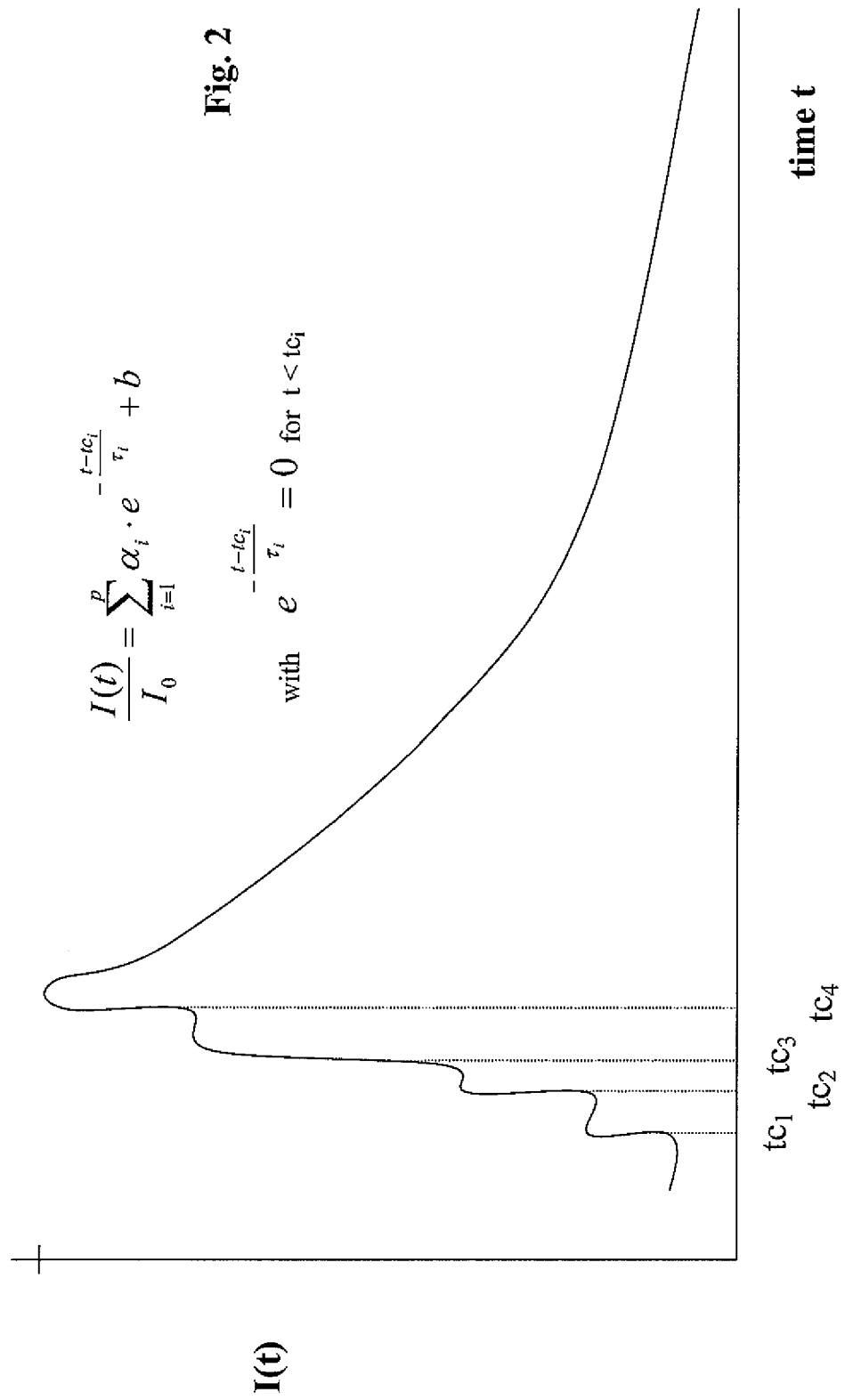
FIG. 2 is a schematic representation of the summary time course of the fluorescence of an object having said fluorescent layers.

By this invention, the increase of the fluorescence intensity is evaluated in detail as a multi-stage course due to the layer-specific fluorescence and each of the four stages in the increasing fluorescence intensity of FIG. 2 reflects the excitation-caused layer-specific fluorescence in the four fluorescent layers 2 of the object 1.

According to the invention, said multi-stage increasing course of the fluorescence intensity is analyzed by determining the times of origin for each of the relevant fluorophores of the layers 2 of the object 1 and by bringing said times of origin into a time-relevant relation to each other.

For the evaluation of the summary fluorescence, the decay behavior of the fluorescence is determined by a calculator 9 and by applying a model function in a in a known manner. According to the invention, the aforementioned times of origin of the single layer-specific fluorophores are considered as parameters in said model function.

Therefore, apart from the parameters lifetime $\tau_i$ and pre-exponential factor $\alpha_i$, a factor $tc_i$, which is to be optimized additionally and marks the time of origin of the fluorescence of the component I, is introduced in the embodiment for a multi-exponential model function for the approximation of the time decay of the fluorescence for each component.

$$\frac{I(t)}{I_0} = \sum_{i=1}^{p} \alpha_i \cdot e^{-\frac{t-tc_i}{\tau_i}} + b \quad (2)$$

with $$e^{-\frac{t-tc_i}{\tau_i}} = 0$$

for $t < tc_i$ and
$I_o$: maximum fluorescence intensity
$I(t)$: fluorescence at time t
$\alpha_i$: pre-exponential factor i
$\tau_i$: decay time of the component i in layer i
$tc_i$: time of origin of fluorescence in layer i
b: underground intensity.

This extended model function makes it possible to obtain a reliable and precise evaluation of a fluorescence progress summarily measured from the fluorescent layers 2 in object 1. The differences of the values $tc_i$ (in the embodiment $tc_1$, $tc_2$, $tc_3$ and $tc_4$) determined in this way indicate the time difference of the origin of the fluorescence in the individual layers 2. If the same values $tc_i$ are determined for several components, a multi-exponential decay behavior exists in the relevant layer.

If each of the values $tc_i$ is multiplied with the light speed in the relevant layer 2 of the object 1, the geometric distances between the fluorescent layers 2 can be calculated on the basis of the obtained product so that conclusions can be drawn on the fluorescence in the individual layers 2 of the object 1. These conclusions are, for example, important for ophthalmologic examinations.

If the equation (2) is used for the evaluation of the decay behavior of the summary fluorescence at each pixel, the location and the distances between the individual layers 2 of the object 1, and thus the geometric structure of the points of origin of the specific fluorophore can be obtained from the values $tc_i$.

Thus, the invention not only allows a precise evaluation of the decay behavior of the summary fluorescence of an object having fluorescent layers, but it makes it also possible to establish the relation between the time-resolved measurement of autofluorescence and the geometric arrangement of the fluorescent layers, in particular for assessing the is metabolic state in the eye, as an equivalent to the optical coherence tomography.

The invention claimed is:

1. A method for determining time-resolved fluorescence in a layer system, comprising:
    applying with a laser a first electro-magnetic radiation to the layer system, wherein a pulse of the laser at a first scan position stimulates a fluorophore in each one layer of multiple layers of the layer system;
    detecting a second electro-magnetic radiation responsive to said first electro-magnetic radiation applied by said laser, wherein said second electro-magnetic radiation is a summary fluorescence, which is a combined responsive fluorescence from said multiple layers of the layer system simultaneously detected in a time domain over a time range in response to said pulse;
    analyzing with a calculator unit rising behavior of the detected summary fluorescence responsive to said pulse over said time range to allocate the detected summary fluorescence into one or more proportions at any given time, after an initial delay each proportion of the one or more proportions at said given time being attributable to a corresponding one layer of the layer system;
    for said each one layer of the layer system identifying a corresponding time delay after which a proportion among said one or more proportions becomes attributable to said one layer; and
    evaluating with a calculating unit a summary decay behavior of the detected summary fluorescence responsive to said pulse by specifying, for said each one layer, the corresponding time delay as a respective, layer-fluorescence, time-of-origin, fit parameter in a model function for approximating a time decay of responsive fluorescence for said each one layer.

2. A method according to claim 1, further comprising calculating a local geometric distance of points of origin of the fluorescence for said each one layer of the layer system by multiplying said corresponding time delay with a light speed.

3. A method according to claim 2, further comprising calculating geometric structures of the layers of the layer system from the local geometric distance of each of the points of origin of the fluorescence for said each one layer of the layer system.

4. A method according to claim 1, wherein said layer system includes structures of an eye.

5. A method according to claim 1, wherein said detecting comprises detecting with a single-photon counting unit in the time domain over the time range in response to said given pulse.

6. A method for determining time-resolved fluorescence in a layer system having multiple layers, comprising:
    applying a pulse of a first electro-magnetic radiation to the layer system;
    detecting a second electro-magnetic radiation, wherein said second electro-magnetic radiation is a summary fluorescence, which is a combined responsive fluorescence from said multiple layers of the layer system simultaneously detected in a time domain over a time range in response to said pulse;

determining a time of origin of the fluorescence in each individual layer of the layer system;

analyzing with a calculator unit rising behavior of the detected summary fluorescence responsive to said pulse over said time range to allocate the detected summary fluorescence into one or more proportions at any given time, after an initial delay each proportion of the one or more proportions at said given time being attributable to a corresponding one layer of the layer system;

evaluating layer-specific, time-dependent parameters for corresponding fluorescence in a model function to approximate a measured summary decay behavior, wherein each of the parameters indicates the time of origin of the fluorescence in a corresponding individual layer of the layer system; and wherein the model function is adjusted to the measurements, including wherein the layer-specific, time-dependent parameters are introduced as fit parameters $tc_i$, in the model function used for the evaluation of the summary fluorescence in the layer system, as a multi-exponential fit according to the general equation (2), $$\frac{I(t)}{I_0} = \sum_{i=1}^{p} \alpha_i \cdot e^{-\frac{t-tc_i}{\tau_i}} + b \tag{2}$$

with $$e^{-\frac{t-tc_i}{\tau_i}} = 0$$

for $t < tc_i$.

* * * * *